United States Patent [19]

Misevich et al.

[11] Patent Number: 5,216,817
[45] Date of Patent: Jun. 8, 1993

[54] DIGITIZER MEASURING SYSTEM

[75] Inventors: Kenneth W. Misevich, Glastonbury, Conn.; Thomas E. Mintel, Rahway, N.J.

[73] Assignee: Colgate-Palmolive Company, New York, N.Y.

[21] Appl. No.: 853,210

[22] Filed: Mar. 18, 1992

[51] Int. Cl.[5] ............................................. A61B 5/103
[52] U.S. Cl. ........................................ 33/515; 33/512; 33/474; 128/774; 128/779; 367/907
[58] Field of Search ................ 33/512, 515, 3 R, 3 A, 33/3 B, 3 C, 459, 460, 474, 203.14; 128/774, 779, 661.03, 660.01, 662.03; 73/632, 644; 364/413.13, 413.25; 367/907, 118

[56] References Cited

U.S. PATENT DOCUMENTS

| | | | |
|---|---|---|---|
| 1,324,624 | 12/1919 | Seay | 33/460 |
| 3,176,263 | 3/1965 | Douglas . | |
| 3,457,647 | 7/1969 | Cohen et al. . | |
| 3,924,450 | 12/1975 | Uchiyama et al. . | |
| 4,220,163 | 9/1980 | Afzali | 128/782 |
| 4,388,831 | 6/1983 | Sherman | 73/632 |
| 4,535,781 | 8/1985 | Hetz | 128/662.03 |
| 4,539,754 | 9/1985 | Antony et al. . | |
| 4,603,254 | 7/1986 | Takano et al. | 364/413.13 |
| 4,603,486 | 8/1986 | Moroney et al. . | |
| 4,604,807 | 8/1986 | Bock et al. . | |
| 4,910,363 | 3/1990 | Koboyashi et al. | 367/907 |
| 4,922,925 | 5/1990 | Crandall et al. | 128/782 |
| 4,956,824 | 9/1990 | Sindeband et al. | 367/907 |
| 4,991,148 | 2/1991 | Gilchrist | 367/907 |
| 5,082,001 | 1/1992 | Vannier et al. | 128/774 |

FOREIGN PATENT DOCUMENTS

| | | | |
|---|---|---|---|
| 0244274 | 11/1987 | European Pat. Off. | 128/774 |
| 61594 | 5/1968 | Fed. Rep. of Germany | 128/774 |
| 2619702 | 3/1989 | France | 128/774 |
| 2641183 | 7/1990 | France | 128/779 |
| 2159943 | 12/1985 | United Kingdom | 128/774 |
| 8802236 | 4/1988 | World Int. Prop. O. | 128/779 |

OTHER PUBLICATIONS

SAC (Scientific Accessories Corp.) graf/pen sonic digitizer, model GP-2-3D.

Primary Examiner—William A. Cuchlinski, Jr.
Assistant Examiner—Alvin Wirthlin
Attorney, Agent, or Firm—Robert C. Sullivan; Richard J. Ancel

[57] ABSTRACT

A system for measurement of the geometries and axes of rotation of an object such as the human body is disclosed. The system includes fixtures which are employed in conjunction with sonic, infrared or other digitizer sources. In the case of the human body, the measurements are made by placing the digitizer sources at locations such as the shoulders, waist and legs to monitor the position of the body during various measuring sequences. The digitizer determines the position of the sources in space by measuring the time for the signal to reach an array of receivers. The fixtures employed in the invention include: a T-square foot reference; a single source digitizing strap; an offset digitizing wand; a base and angle fixture; a foot and hip rotation fixture; an ankle axis practice fixture; and an umbilicus reference bar.

2 Claims, 9 Drawing Sheets

DIGITIZER MEASURING SYSTEM

BACKGROUND AND SUMMARY OF THE INVENTION

The present invention relates to geometries of an object, such as the human body, with a three dimensional (3-D) sonic digitizer. With regard to the human body, these geometries include: upper body landmarks such as the shoulder, spine and hip; lower body axes and lengths; and foot landmarks.

The measurements are made by placing sonic or other digitizer sources at locations such as the shoulders, waist and legs to monitor the position of the body during various measuring sequences. The sonic digitizer determines the position of the sources in space by measuring the time for the sound to reach an array of microphones. In another embodiment, infra red digitizer sources may be employed.

The basic anthropometric information required to model the foot system and specify the shoe/foot system for shoe design criteria is obtained by use of the present measuring system, sometimes referred to herein as "BioExam". The present system is intended to be as computerized and streamlined as possible so that a large data base can be generated easily and population segments can be established.

Previous systems for measuring the dimensions of various objects are described in the following U.S. Pat. Nos.: 3,176,263 to Douglas; 3,457,647 to Cohen et al.; 3,924,450 to Uchiyama et al.; 4,539,754 to Antony et al.; 4,603,486 to Moroney et al.; and 4,604,807 to Bock et al. These U.S. Pat. Nos. are incorporated herein by reference.

By the present invention, all 3-D coordinates and axes are referenced to a movable reference system, called the T-Square coordinate system, which rests on the horizontal plane of the global or laboratory based coordinate system of the 3-D digitizer. Data taken into the digitizer in base coordinates is therefore transformed into the T-Square coordinate system.

All measurements may be performed, for example, with a plurality of sonic sources which may be connected appropriately to the digitizer, through use of a color coding system.

Generally, the subject is either stabilized to minimize extraneous movement to within acceptable limits, or the body is monitored for movement during the test sequence.

The T-Square references the foot position by repeatably contacting three points: the rear of the heel, the lateral malleolus and the lateral side of the sole of the foot.

Body and foot landmarks are located with a measuring wand which is formed by two sources and a measuring tip, all in linear alignment. Measurements are taken while the tip rests on the point to be measured with the 3-D coordinates accepted only after the standard deviation of the data is less than a predetermined standard such as 0.7 millimeter.

Axes are measured by swinging the appropriate body segment through an arc in space, finding the plane of the arc and then referencing the axis to the T-Square coordinate system.

The present invention provides a method of measurement which includes protocols, analyses and fixtures.

In one embodiment, the invention is intended to supply basic anthropometric information required to model the foot system and, further, to supply design criteria for the shoe/foot system. In addition, the invention has the capability to systematically gather data into a streamlined computer data base in a rapid and efficient manner in order to establish shoe design criteria for the general population.

Only in the last 15 years or so has the ability to measure motions in 3-D space become routinely available. Most of the systems, however, have been very elaborate, cumbersome and expensive. By the present invention, with the use of relatively inexpensive digitizers such as 3-D sonic digitizers, the analyses and protocols for rapid body measurements have now been developed.

The BioExam system of the present invention differs from previous systems because of the unique fixtures, software algorithms, and protocols which may be combined to make the various tests as streamlined and comfortable as possible. A time period of approximately fifteen minutes is all that is required to collect and analyze 3-D data for the feet base and angle, upper body, feet morphology, ankle axes, knee axes, hip axes and hip rotation.

DESCRIPTION OF THE PREFERRED EMBODIMENTS

Figures 1, 2, 3, 4, 5:
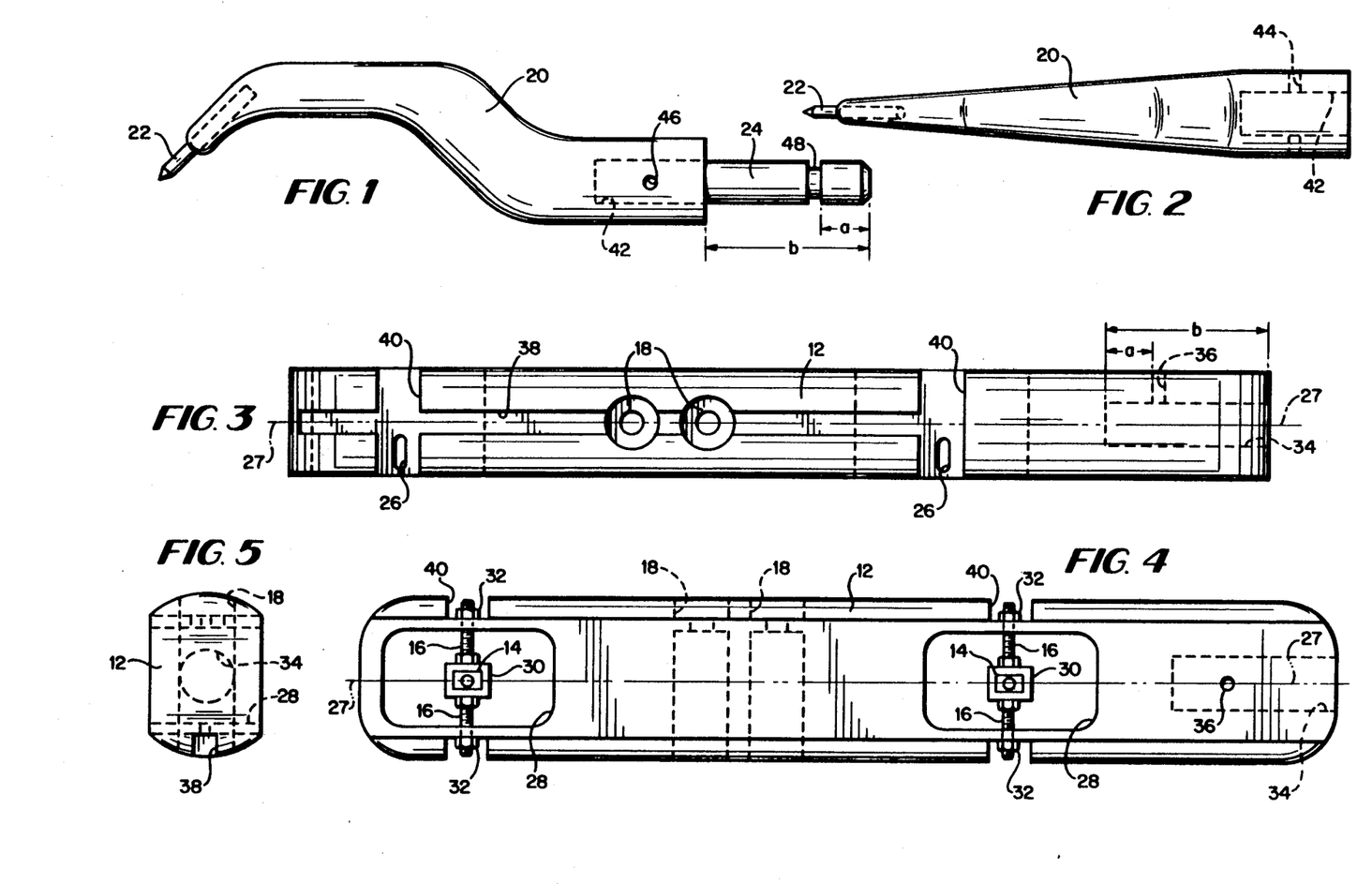
FIG. 1 is an elevational view of the digitizer wand tip employed in the present invention.
FIG. 2 is a top plan view of the digitizer wand tip of FIG. 1.
FIG. 3 is an elevational view of the digitizer wand handle of the present invention.
FIG. 4 is a top plan view of the digitizer wand handle of FIG. 3.
FIG. 5 is an end view of the digitizer wand handle of FIG. 3.

In FIGS. 1 through 5, a digitizing wand is shown having a tip body 20 as shown in FIGS. 1 and 2 and a wand handle 12 as shown in FIGS. 3 through 5. The wand tip body 20 has a wand tip 22 used in taking measurements which aligns with two digitizing sources 14 on the wand handle 12. The wand tip body 20 is curved so that the wand tip 22 can reach an object to be measured which does not have a direct line of sight to the receivers.

The wand tip body 20 also contains a wand tip alignment pin 24 secured into an alignment pin slot 42 at the end of the tip body 20 by an alignment pin 46 which enters through a locking pin slot 44 on the side of the wand tip body 20. An alignment pin groove 48 is also located at the end of the wand tip body 20 for locking into the wand handle 12.

In FIGS. 3 through 5, the wand handle 12 is shown having two digitizing sources 14 secured onto mounting plates 30 within separate digitizing source cavities 28 by threaded rods 16 and alignment lock nuts 32 at both ends of each digitizing source 14. The lock nuts 32 are located within slots 40 on the sides of the wand handle 12. The digitizing sources 14 may be positioned within the slots 40 by adjustment along the digitizing source alignment slots 26, also located within the slots 40 as shown in FIG. 3. Thus the digitizing sources 14 may be aligned with respect to the longitudinal centerline 27 of the handle 12.

The wand handle 12 is provided with two switch installation cavities 18 positioned between the digitizing sources 14 and accessed by a wiring slot 38. Switches are installed within these cavities to activate the digitizing sources 14 and act as a switch to close the keyboard from the digitizing system. At the end of the wand handle 12 is located an alignment pin slot 34 for receiving the alignment pin 24 of the wand tip body 20. Once the alignment pin 24 is positioned inside the alignment pin slot 34, a set screw 36 is engaged at the top of the wand handle 12 so as to contact the alignment pin groove 48. This locks the wand tip body 20 into the wand handle 12 so that both components are fixed together but the tip body 20 can rotate relative to the wand handle 12.

Figure 6:
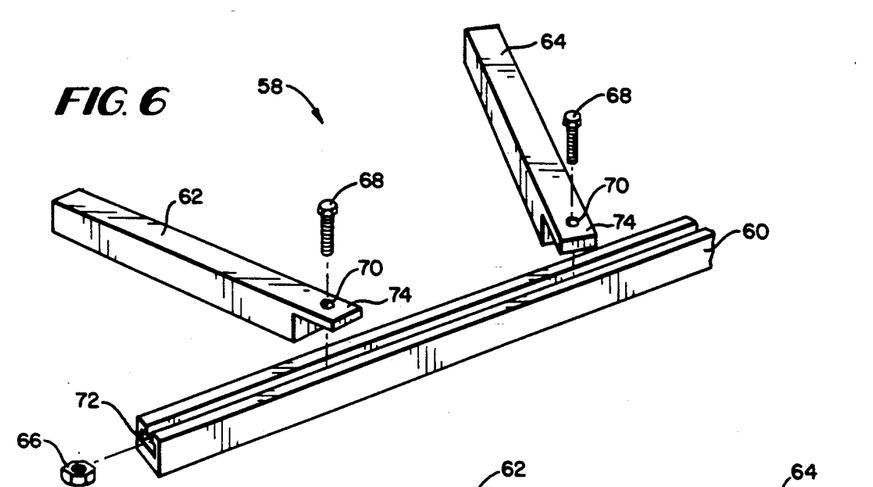
FIG. 6 is a perspective view of the base and angle fixture employed in the present invention.
Figure 7:
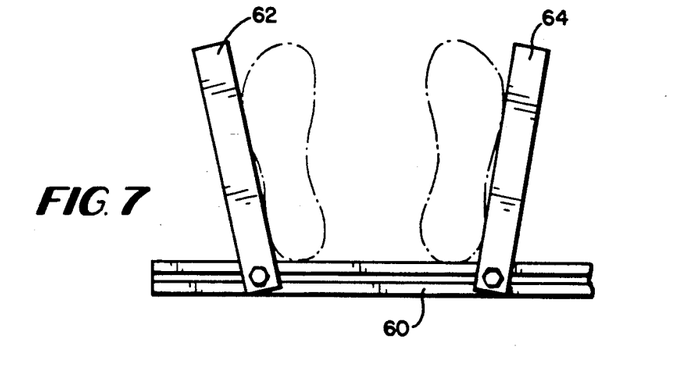
FIG. 7 is a top plan view of the base and angle fixture of FIG. 6.

In FIGS. 6 and 7 is shown the base and angle fixture 58 used to uniformly or repeatably recreate the foot positions used for various parts of the test. A left and right foot angle reference 62, 64 are used to mark the position of the foot against the reference base 60. Both angle references 62, 64 have mounting flanges 74 at one end with a hole 70 drilled through each mounting flange 74 for receiving a bolt 68. The reference base 60 has a T-slot 72 for receiving angle reference lock nuts 66. A bolt 68 is passed through the hole 70 in the mounting flange 74 of each angle reference 62, 64 and threadedly engages an angle reference lock nut 66 within the T-slot 72 of the reference base 60. This allows the foot positions to be recreated for use throughout the test.

Figure 8:
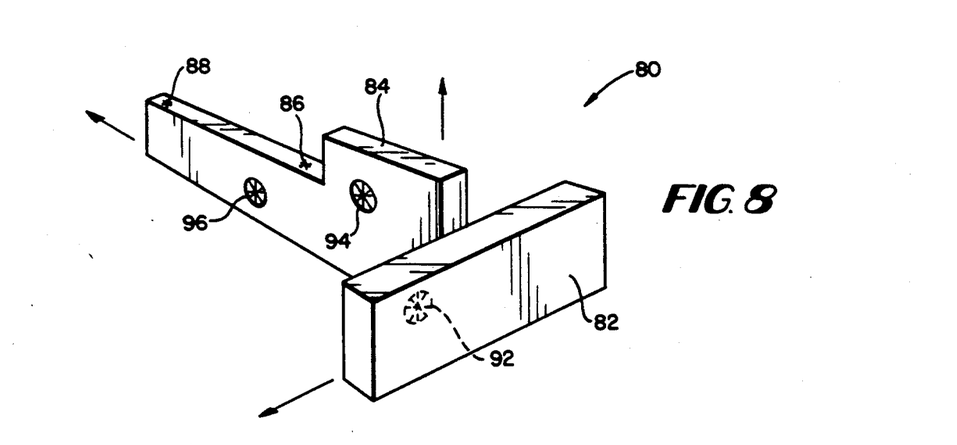
FIG. 8 is a perspective view of the T-square fixture employed in the present invention.
Figure 9:
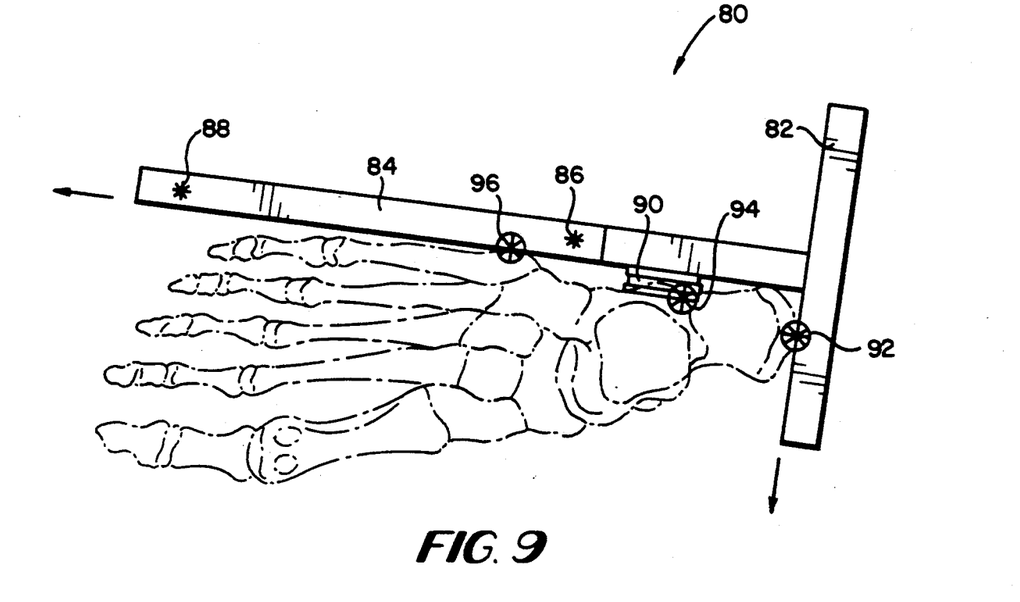
FIG. 9 is a top plan view of the T-square fixture of FIG. 8.
Figure 10:
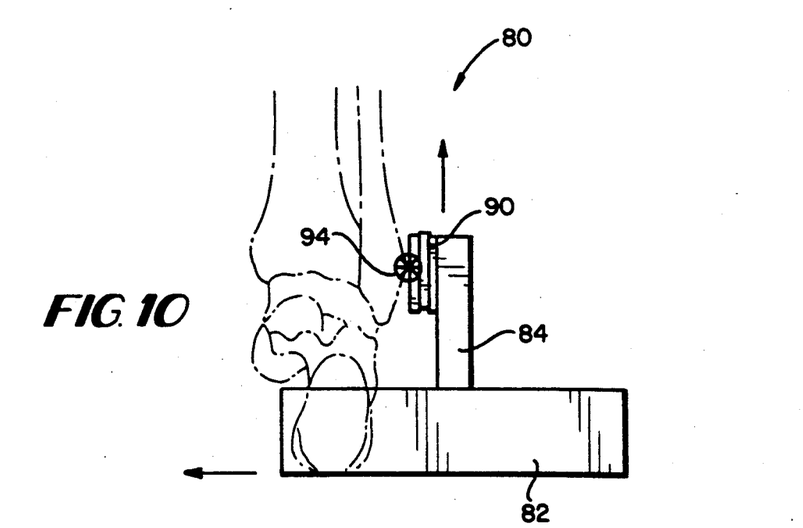
FIG. 10 is an end view of the T-square fixture of FIG. 9.

FIGS. 8 through 10 show a T-square fixture 80 which allows quick and precise alignment of the foot into a movable repeatable reference coordinate system. Using a heel reference plate 82 attached to a lateral reference plate 84, three fixed positions of the foot may be recorded: the lateral reference plane 96, the heel reference plane 92, and the lateral malleolus reference plane 94. If necessary, lateral malleolus spacers 90 are used to obtain the lateral malleolus reference plane 94. The spacers 90 also are used to maintain the foot in an initial stance position with respect to subtalar axis orientation, e.g., tibia with respect to the foot, throughout the course of the test sequence. A front digitizing source 88 is located on the top of the lateral reference plate 84 at the front of the plate 84 and a rear digitizing source 86 is located on the top of the lateral reference plate 84 near the center portion of the plate 84, as shown in FIGS. 8 and 9. When the T-square fixture 80 is properly positioned with reference planes against, or touching the foot to establish the three points of contact 92, 94, 96, the front and rear digitizing sources 86, 88 are activated. The computer then records these signals to establish global 3-D coordinates of the T-square fixture 80 such that all future global or laboratory measurement coordinates are mathematically transformed into the T-square coordinate system.

Upon establishing the coordinates as stated above, the T-square 80 may then be removed and the digitizer wand 10 is employed to digitize the foot while the foot remains in the position at which it made 3-position contact with the T-square 80. Thus the three dimensional morphology of the foot has been defined.

Figures 11, 12:
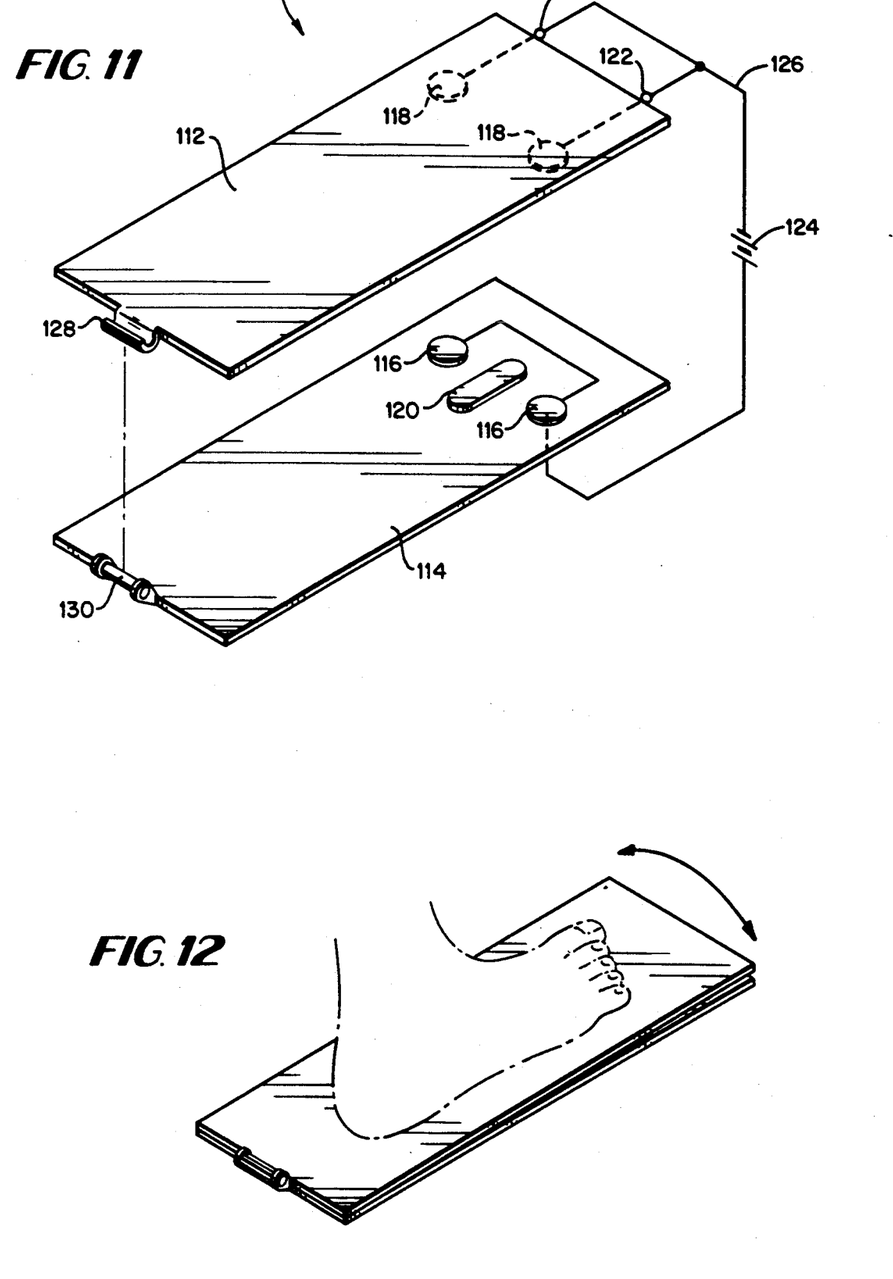
FIG. 11 is an exploded perspective view of the ankle axis practice fixture employed in the present invention.
FIG. 12 is a perspective view showing the ankle axis practice fixture of FIG. 11 in an operating position.

FIGS. 11 and 12 show an ankle axis practice fixture 110 which is used to practice the bodily motion which will define the ankle axis such that the foot will remain in proper position throughout flexing of the tibia about the ankle axis. The ankle axis practice fixture 110 contains an upper plate 112 hingedly joined to a lower plate 114 at one end of the plates 112, 114 by upper and lower plate hinge members 128, 130. The lower portion of the upper plate 112 rests on a centering fulcrum 120 centered in the upper portion of the lower plate 114. Lower circuit contact points 116 are located on either side of the centering fulcrum 120 on the lower plate 114 such that, when the foot leans to one side or the other, one of the upper circuit contact points 118 on the upper plate 112 will contact a lower circuit contact point 116. This will form a complete circuit as electrical wiring 126, connecting a power source 124 and the upper and lower circuit contact points 118, 116 will energize a circuit feedback device 122 such as an LED display or a buzzer to indicate that the subject is not properly balanced. The goal is for the subject to be able to flex his/her knee and try to prevent making contact on either side.

Figure 13:
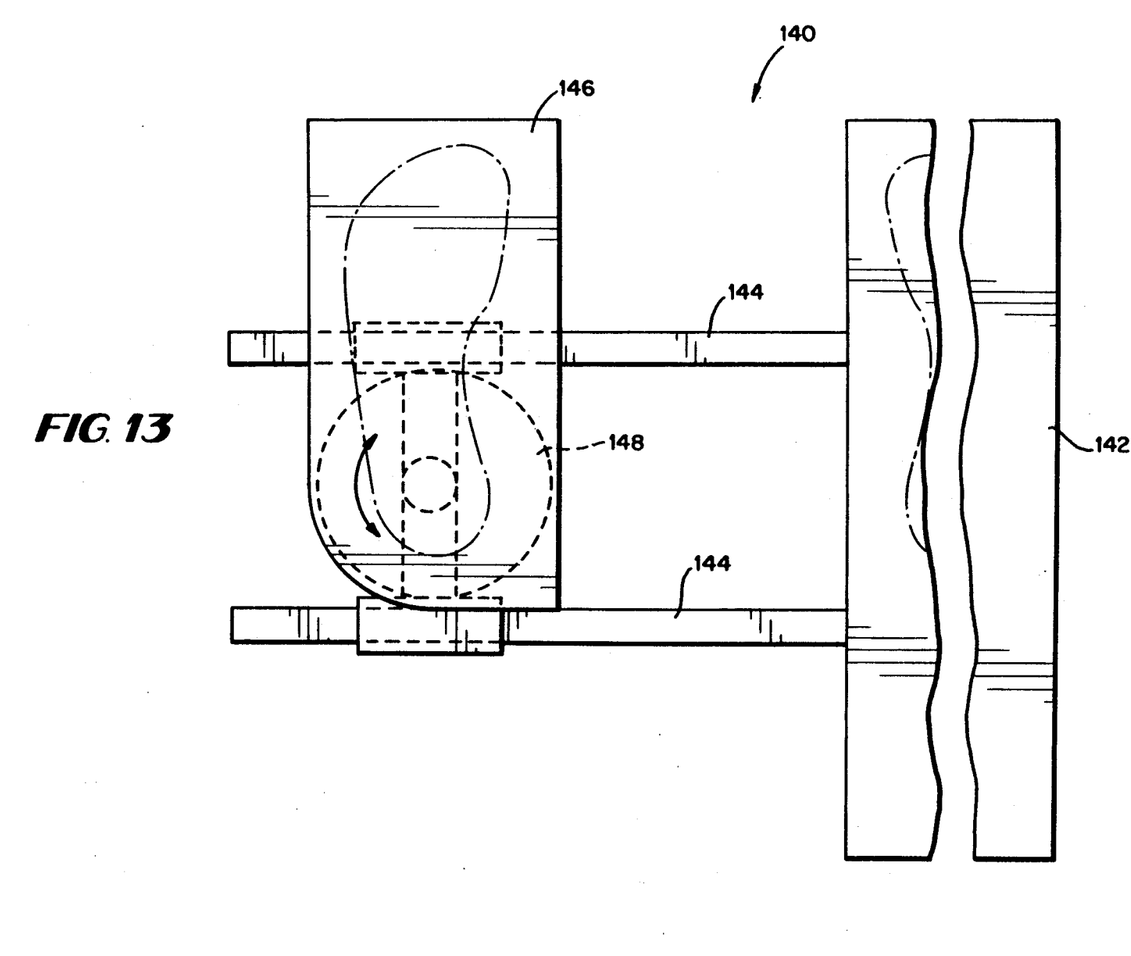
FIG. 13 is a top plan view of the foot and hip rotation fixture of the present invention.
Figure 14:
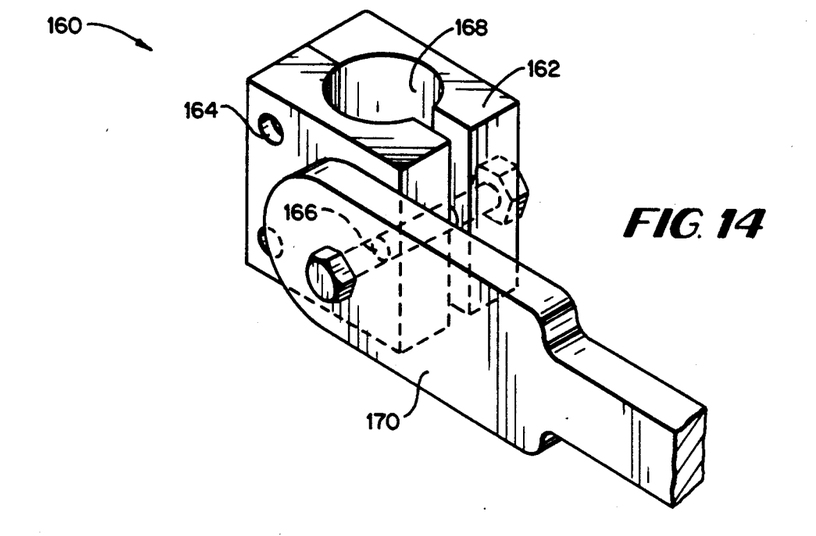
FIG. 14 is a perspective view of the stability bar collar employed in the present invention.
Figure 15:
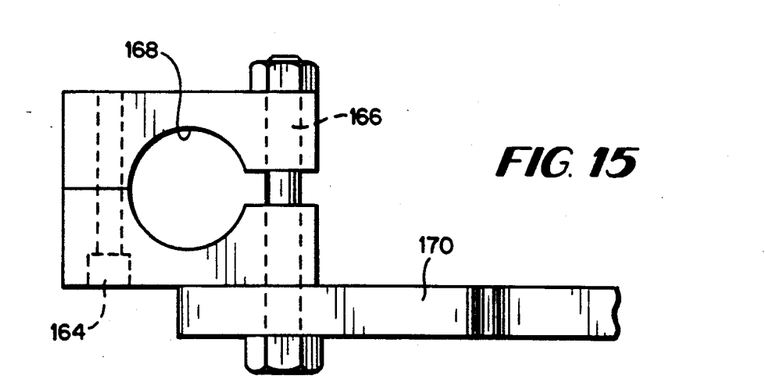
FIG. 15 is a top plan view of the stability bar collar of FIG. 14.
Figure 16:
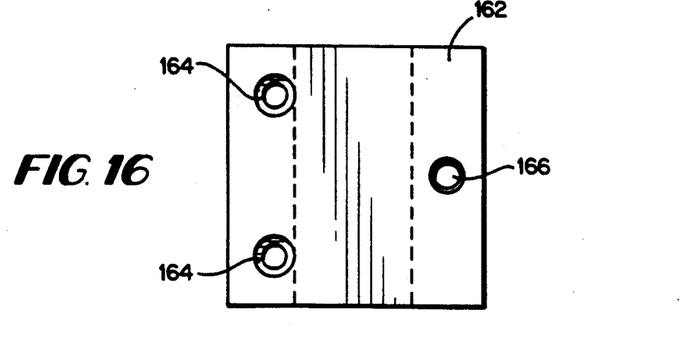
FIG. 16 is an elevational view of the stability bar collar of FIG. 14.
Figure 17:
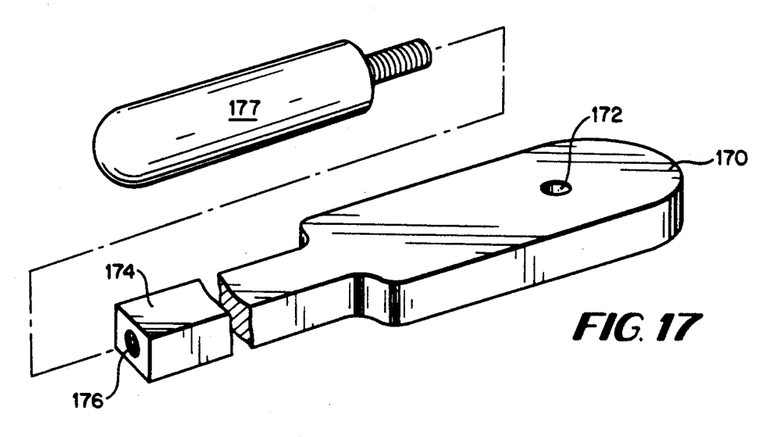
FIG. 17 is a perspective view of the umbilicus reference fixture employed in the present invention.
Figure 18:
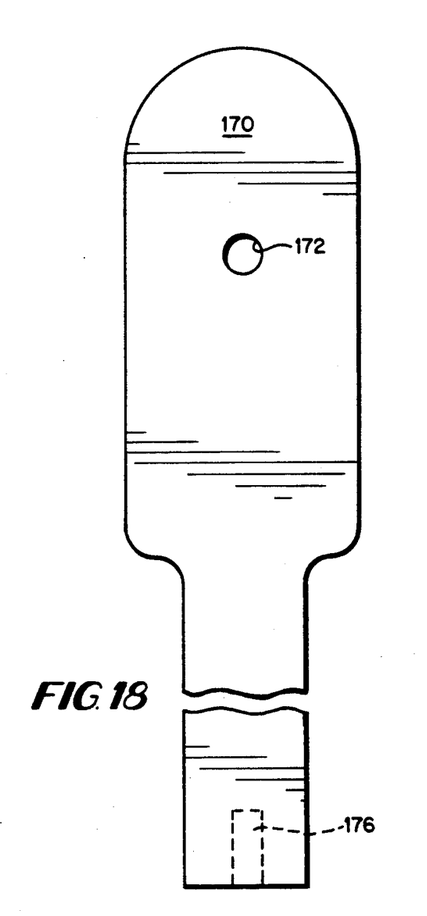
FIG. 18 is a top plan view of the umbilicus reference fixture of FIG. 17.
Figure 19:
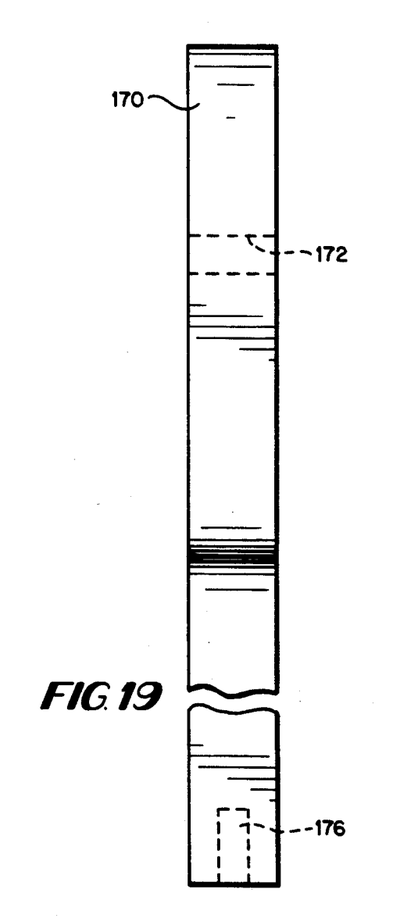
FIG. 19 is an elevational view of the umbilicus reference fixture of FIG. 17.

FIG. 13 shows a left foot and hip rotation fixture 140 used to determine the range of motion and joint distraction possible. A rotatable plate or lazy susan 148 is positioned between two guide rails 144 so as to prevent movement of the lazy susan 148 transversely. A rotation foot plate 146 is movable inwardly or outwardly between guide rails 144 to accommodate the stance of a particular person. By placing the heel of one foot in the center of the lazy susan 148 axis, the other foot on a fixed foot plate 142, and the T-square fixture of FIG. 8 in position against the foot on the lazy susan, the digitizing computer can record the maximum internal and external angles made as the foot is rotated. Upon lifting and repositioning the lazy susan 148, the other foot can be tested as well.

FIGS. 14 through 19 show an umbilicus reference fixture 160 which allows positioning of the subject repeatably for measurement of the upper body, knee, and hip axes. A stability bar collar 162 contains two halves which, when joined together, form an opening 168 for receiving a fixed floor or laboratory based support. The stability bar collar 162 also has two holes 164 for receiving clamping bolts to clamp the back end of the collar 162 together and a hole 166 for receiving an adjustment bolt, which attaches the reference bar 170 to the umbilicus reference fixture 160. The reference bar 170 contains a reference arm 174, a mounting hole 172 to be used in the connection of the umbilicus reference fixture 160, and a threaded portion 176 for receiving an umbilicus pointer 177. In the use of the device 160, the subject is positioned so as to come into contact with umbilicus pointer 177 at the umbilicus or navel, thus establishing a reference point for measurement.

Figure 20:
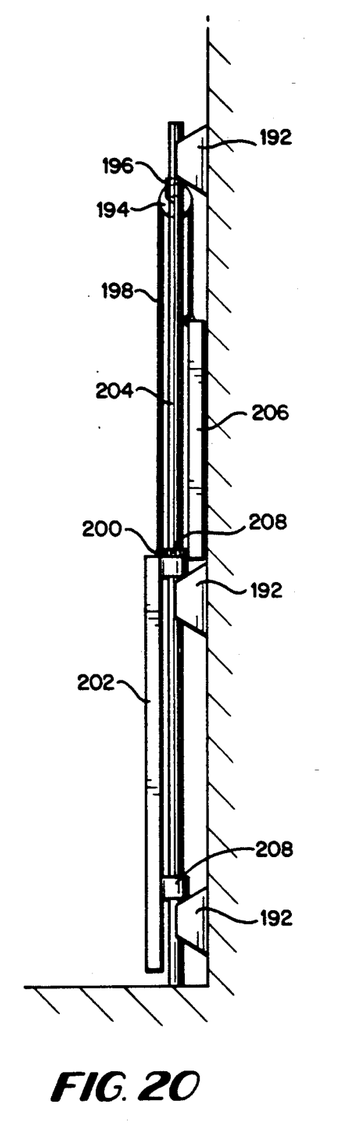
FIG. 20 is a side elevational view of the digitizer wall mount employed in the present invention.
Figure 21:
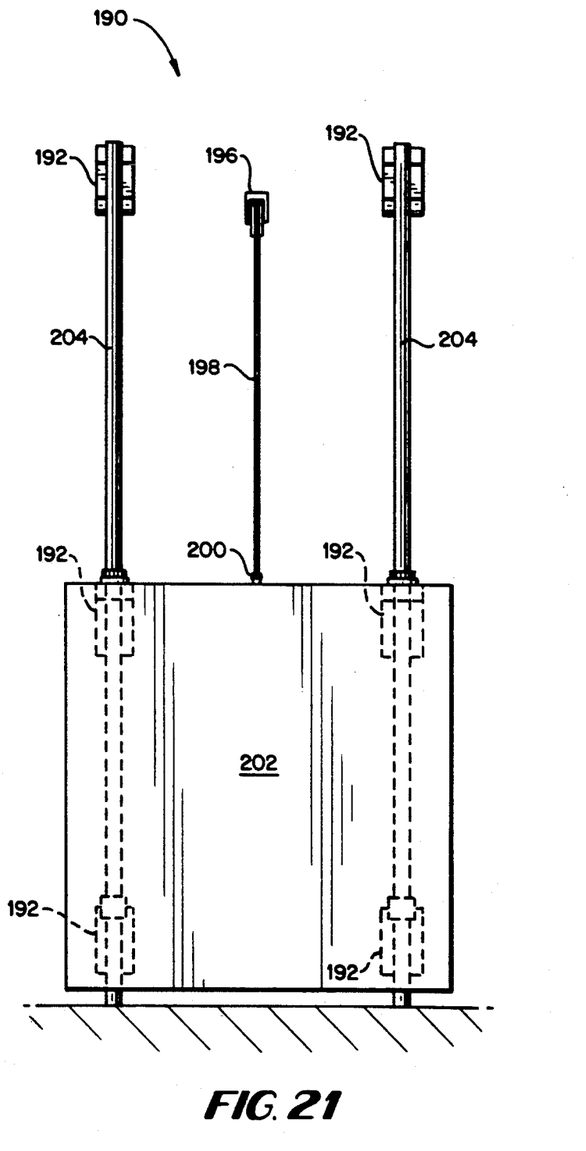
FIG. 21 is a front elevational view of the digitizer wall mount of FIG. 20.

FIGS. 20 and 21 show a digitizer wall mount 190 with rail mounting blocks 192 to support guide rails 204 upon which is mounted the digitizing board 202 which receives signals from various digitizing sources. In one embodiment, the digitizer determines the position of sources in space by measuring the time it takes for sound to reach an array of microphones. The digitizing board 202 may be raised and lowered through the use of a pulley system containing a pulley 194 mounted to a pulley mounting block 196 at the top of the wall mount 190, along with a cable 198 and a counterweight 206. Bushing blocks 208 are used to guide the digitizing board along the guide rails 204. An eyelet 200 is also located at the top of the digitizing board 202 for connection to the cable 198.

Figure 22:
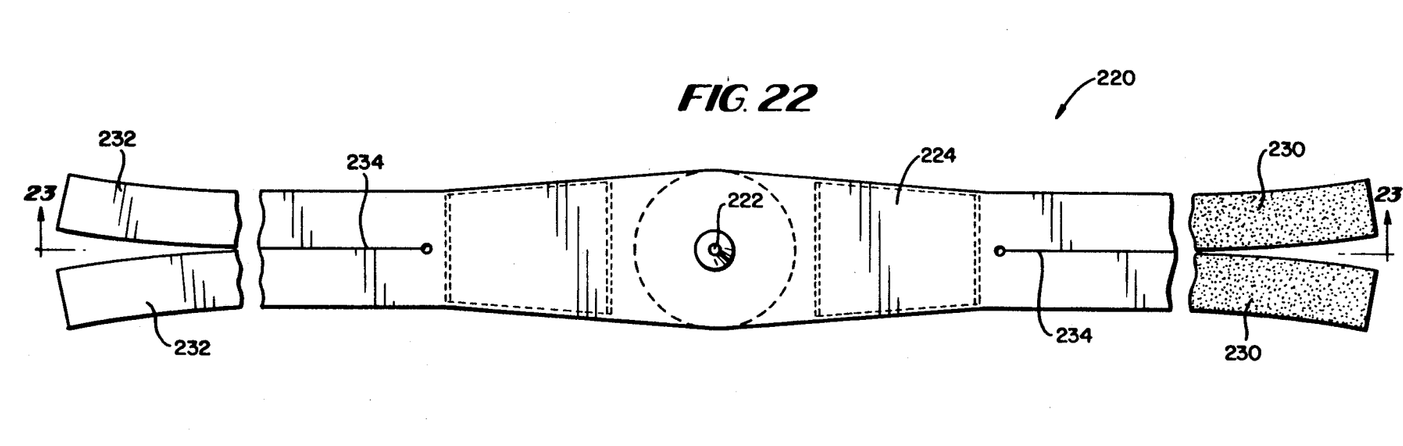
FIG. 22 is a top plan view of the digitizer source holder straps employed in the present invention.
Figure 23:
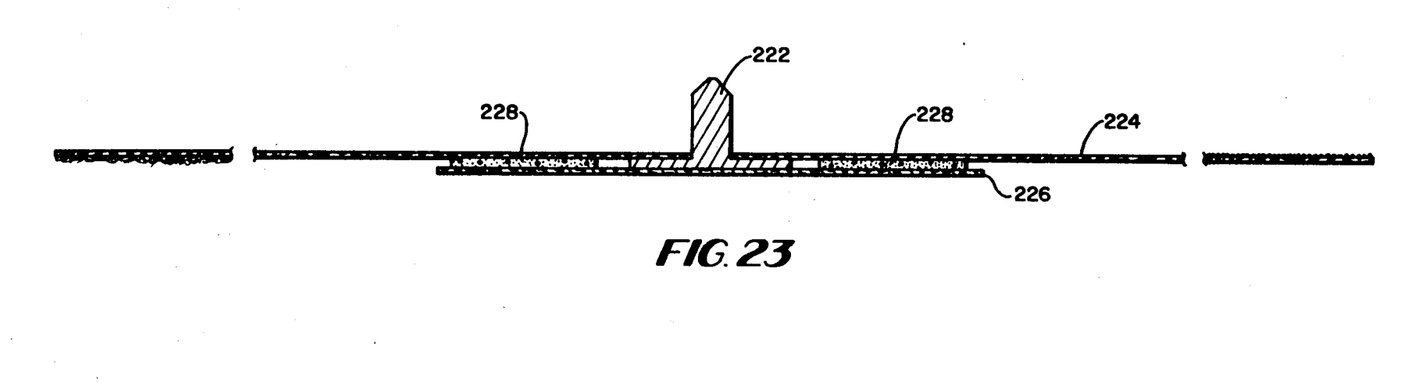
FIG. 23 is a cross sectional view taken along line 23—23 of FIG. 22.

FIGS. 22 and 23 show a digitizer source holder strap 220 for holding the digitizing source 222 during operation. The strap 220 contains a main strap member 224 separated from the digitizing source holder strap 226 by a foam separator 228. At both ends of the strap 220 is a parting slit 234 which divides each end of the strap into two securing members such as velcro securing members 230, 232.

In one embodiment, the present measuring system is composed of a multipoint 3-D digitizer, a computer for collection of the data and a set of reference fixtures which allow the data from each test sequence to be related to a spatial coordinate system referenced to the foot. Also a set of protocols with specific body positioning and referencing sequences has been developed.

Separate test data for each individual are accumulated in Bio-Exam data bases and are directly interactive with a demographic data base which may be created through the use of questionnaires.

The tangible features of the Bio-Exam include:

1. T-Square Foot Reference—This device allows quick and repeatably accurate alignment of the foot into a movable reference coordinate system. It is based on the positions of the back of the heel, the lateral border and the lateral malleolus. In addition, spacers at the malleolus maintain the foot in a constant stance position throughout the course of the test sequence.

2. Offset Digitizing Wand Since the digitizer requires a line of sight path between the source and the receivers, points out of sight cannot be digitized. The wand consists of two sources placed in a straight line with the extended tip which can reach behind an object.

3. Additional components include a base and angle fixture which is essential to recreating the foot positions for various parts of the test, a foot and hip rotation fixture, an ankle axis practice fixture and a reference bar called "Umbilicus Reference" which allows positioning of the subject repeatably for measurement of the upper body, knee and hip axes.

The construction of all of the fixtures may be modified, as long as the fixtures accomplish their original purpose. Thus, for example, the T-Square can be designed to reference against different points on the foot, but at least three fixed, easily found reference points must be used to satisfy this criterion. Also, the wand can be changed as long as the two sources and pointer tip are collinear and the two sources always have a direct line of sight to the receivers. It is noted that it is possible to employ three or more sources. In addition, the order in which the test sequence is performed can be altered as long as the information is stored in the appropriate data bases.

By the use of an arc/axis method in accordance with the present invention, the axis of a loaded or unloaded joint is determined in the 3-D T-square coordinate system using only a single source and monitor reference sources for extraneous body motion. This is done by swinging an arc in a plane. This method has not been used before because it was not believed to be possible.

By using the arc/axis method described above in conjunction with software, there is no need for a synchronous multichannel 3-D digitizer thereby reducing the cost requirements of the hardware tremendously.

The system is constructed in a way that allows for rapid computerized data acquisition which in turn generates the information and statistics necessary to model the human foot and design ideal footwear based on these values.

The integration with demographic data bases allows populations to be segmented by the functional use of the foot. Therefore, footwear can be optimized for any specific use and requirement of the foot.

In measuring the various geometries of a subject, it is important that the subject establish a comfortable natural stance to maximize stability during the testing procedure and also to provide a repeatable reference to the T-square and possibly allow future morphological correlation. Thus, facing the digitizer, the subject finds a natural stance by rocking from foot to foot such as if preparing to hit a golf ball. The base and angle fixture positions are then set on the lateral borders of the feet with the rear of the heel in contact. After setting these positions, the fixture is locked. With no subject movement, the base and angle fixture is removed and the T-square is placed against the reference positions of the right foot. With a suitable marking instrument, such as a water based ink marker, the operator should mark the center of the achilles and the T-square. The wand is then employed to digitize the medial malleolus. Next, the T-square is moved away and the lateral malleolus is digitized. A mark is then placed on the shin in the center of the achilles and also one inch above and below the first mark. This procedure is then repeated for the left foot. The magnetic T-square spacers are inserted in accordance with instructions from the computer.

For further measurements, the base and angle fixture will determine the stance of the subject.

With regard to upper body landmarks, the next procedure is employed to determine essential upper body anthropometry and symmetry for demographic information and correlation to lower body dimensions and axes. In carrying out this procedure, strap sources are placed on the back of the subject, red on the right side and green on the left. While explaining the need for no movement during this test, the operator sets the height of the umbilicus reference and allows the subject to come into natural contact. Any movement will require repeat measurements. While maintaining the umbilicus contact, the subject will then be instructed to rock gently into the base and angle fixture. The subject should be instructed to stand still, arms relaxed at the side and looking straight ahead. The operator will then quickly digitize the following: top of the head; right shoulder (acromion process); C-7 cervical protuberance; maximum convex point of the dorsal spine; maximum concave point of the lumbar spine; right anterior superior iliac spine; left shoulder (acromion process); and left anterior superior iliac spine. The subject is then instructed to step away with the source facing the digitizer board and the umbilicus stabilizer tip is then digitized.

With regard to measurement of foot landmarks, in order to measure the basic geometry of the foot, a bench is set into a marked location and the subject is instructed to place the right foot on a foot print, followed by loading of the leg with a straight arm while a vertical position is set. The leg should be bent and loaded on top of the knee. The subject uses a railing for stability. The operator will then quickly digitize the following: center of mark on T-square for x value only; achilles marks including low, middle and high; center of instep, including low, middle and high; navicular protuberance mark; side of first metatarsal head; side of fifth metatarsal head; tuberosity of fifth metatarsal mark; marks on the metatarsal head (first through fifth); tissue between the toes (one through five); centers of toe ends (one through five); and medial and lateral heel fat pads (for width determination only). This procedure is then repeated for the left foot.

With regard to hip rotation, the following procedure is carried out in order to establish the range of motion about the hip joint axis along the leg in a vertical axis to correlate to body asymmetries. The hip rotation fixture is placed in the marked space for the right leg test. Facing the digitizer, the subject places the right foot in the center of the lazy susan device, and the other foot is then set with the base and angle fixture., Next, the T-square is placed in position on the rotating foot. With a digitizing source placed on the hip on the contralateral side, the subject then rotates a stiff leg to the extreme range of motion, with internal/external rotation. The computer will monitor the digitizing source on the hip and signals any movement. Several rotations should be carried out to allow proper monitoring and reduction of data by the computer. The procedure is then repeated for the left leg.

Additional protocols are then carried out for each of the following: the ankle axis; the knee axis; and the hip axis.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A system which provides physical data sufficient for mechanical structural analysis of an object, comprising:

means for aligning the object into a movable repeatable reference coordinate system;

means for providing a point source of energy which locates a point on said object with respect to said reference coordinate system, said energy providing means including a wand member having a tip portion in alignment with said energy source; and means for receiving said energy at a predetermined location;

wherein the object aligning means includes a T-square fixture which allows quick and precise alignment of the foot into a movable repeatable reference coordinate system, said T-square fixture having a heel reference plate secured to a lateral reference plate and providing reference points for contact with a lateral reference point, a heel reference point and a lateral malleolus reference point, and further including front and rear digitizing sources located on the lateral reference plate.

2. A system which provides physical data sufficient for mechanical structural analysis of an object, comprising:

means for aligning the object into a movable repeatable reference coordinate system;

means for providing a point source of energy which locates a point on said object with respect to said reference coordinate system, said energy providing means including a wand member having a tip portion in alignment with said energy source; and means for receiving said energy at a predetermined location;

wherein the object aligning means includes an ankle axis practice fixture for use in defining the ankle axis, said fixture having an upper plate hingedly joined to a lower plate, with the lower portion of the upper plate resting on a centering fulcrum centered in the upper portion of the lower plate, and further including circuit contact points on either side of the centering fulcrum on the lower plate and with upper circuit contact points on the upper plate for contacting the lower plate contact points when the upper plate rotates to one side or the other during use.

* * * * *